(12) United States Patent
Sideris

(10) Patent No.: US 7,425,251 B2
(45) Date of Patent: *Sep. 16, 2008

(54) SYSTEM AND METHOD

(75) Inventor: Dimitrios Sideris, London (GB)

(73) Assignee: Deltadot Ltd, London (GB)

( * ) Notice: Subject to any disclaimer, the term of this patent is extended or adjusted under 35 U.S.C. 154(b) by 641 days.

This patent is subject to a terminal disclaimer.

(21) Appl. No.: 10/344,070

(22) PCT Filed: Jul. 20, 2001

(86) PCT No.: PCT/GB01/03286

§ 371 (c)(1),
(2), (4) Date: Jun. 27, 2003

(87) PCT Pub. No.: WO02/13122

PCT Pub. Date: Feb. 14, 2002

(65) Prior Publication Data

US 2004/0014231 A1 Jan. 22, 2004

(30) Foreign Application Priority Data

Aug. 8, 2000 (GB) ................................. 0019499.3

(51) Int. Cl.
*G01N 27/447* (2006.01)
*G01N 27/453* (2006.01)
*G01N 30/02* (2006.01)
*G01N 33/48* (2006.01)

(52) U.S. Cl. .................. 204/450; 205/452; 205/603; 205/600; 422/70; 702/19

(58) Field of Classification Search .................. 204/450, 204/600, 603, 612, 461, 452; 422/70; 702/19–22
See application file for complete search history.

(56) References Cited

U.S. PATENT DOCUMENTS

| | | | |
|---|---|---|---|
| 5,114,551 | A | 5/1992 | Hjerten et al. |
| 5,141,609 | A | 8/1992 | Sweedler et al. |
| 5,627,643 | A | 5/1997 | Birnbaum et al. |
| 6,017,435 | A | 1/2000 | Hassard et al. |
| 6,103,533 | A | 8/2000 | Hassard et al. |

FOREIGN PATENT DOCUMENTS

| | | |
|---|---|---|
| GB | 2 259 980 | 3/1993 |
| WO | WO 96/35946 | 11/1996 |

(Continued)

OTHER PUBLICATIONS

International Search Report for International Application No. PCT/GB01/03286 filed Jul. 20, 2001, mailed Mar. 25, 2002.

(Continued)

*Primary Examiner*—Alex Noguerola
(74) *Attorney, Agent, or Firm*—Ungaretti & Harris LLP

(57) ABSTRACT

A system and method of characterizing, in particular sequencing, polymeric samples, the system comprising: a space-time map generator for generating a space-time map of points representative of the signal peaks of signals detected at a plurality of spaced positions as passed by the migrating components of a plurality of separately-provided sample plugs; and a vertex finder for identifying vertices from the space-time map, with a single vertex being identified for the components of each separately-provided sample plug and the velocities of the sample components being determinable from the points in the space-time map.

25 Claims, 3 Drawing Sheets

FOREIGN PATENT DOCUMENTS

WO      WO 98/49548      5/1998
WO      WO 98/45948      10/1998

OTHER PUBLICATIONS

S.X. Lu et al., "Side-entry Excitation and Detection of Square Capillary Array Electrophresis for DNA Sequencing," A Journal of Chromarography, Aug. 20, 1999, pp. 359-369, vol. 853, No. 1-2.

M. Neumann et al., "Capillary Array Scanner for Time-resolved Detection and Intification of Fluorescently Labelled DNA Fragments," A Journal of Chromatography, Feb. 25, 2000, pp. 299-310, vol. 871, No. 1-2.

M.R. Alward, "Trends in DNA Genotyping," Trac, Trends in Analytical Chemistry, May 1, 1997, p. IX, vol. 16, No. 5.

SYSTEM AND METHOD

The present invention relates to a system for and method of characterising, in particular sequencing, polymeric samples, in particular, but not exclusively, as measured electrophoretically. The technique of the present invention is the MITSO™ characterisation technique.

Electrophoretic separation techniques are separation techniques in which the components of a sample plug are separated in a separation column by the differences in the migration rates of those sample components on the application of an electric field therealong, where absorption, fluoroescence, electrochemistry, conductivity, radioactivity and mass spectrometry can be all used to detect the electrophoretic separation.

By way of example, DNA samples are commonly characterised by Sanger sequencing. Whilst Sanger sequencing is in common use, the technique is limited in a number of respects, not least because the DNA bands have to be labelled according to base pair termination.

It is an aim of the present invention to provide an improved system for and method of characterising in particular sequencing, polymeric samples, such as DNA samples, which can be used with both labelled and non-labelled sample components.

Accordingly, the present invention provides a system for characterising, in particular sequencing, polymeric samples, comprising: a space-time map generator for generating a space-time map of points representative of the signal peaks of signals detected at a plurality of spaced positions as passed by the migrating components of a plurality of separately-provided sample plugs; and a vertex finder for identifying vertices from the space-time map, with a single vertex being identified for the components of each separately-provided sample plug and the velocities of the sample components being determinable from the points in the space-time map.

Preferably, the system further comprises a velocity sorter for determining the nominal velocities associated with the signal peaks in the signals and grouping those signal peaks into sets according to nominal velocity.

Preferably, the space-time map generator is configured to utilise a corrected time component in generating the space-time map according to a function of the electric current variation.

More preferably, the correction is according to the function $t_c = \int I_0/I(t')dt'$ in the range of 0 to t, where t is the measured time, $t_c$ is the corrected time, I is the measured current and $I_0$ is the reference current.

Preferably, the space-time map generator is an equiphase space-time map generator for generating an equiphase space-time map of equiphase points.

More preferably, the equiphase space-time map generator is configured to transform each data set into a set of local slopes and determine the local minima as the minimum absolute local derivatives.

In one embodiment the components are non-labelled.

In another embodiment the components are labelled.

Preferably, the components are migrated through a channel.

More preferably, the channel comprises a separation channel through which the components are electrophoretically driven.

Preferably, the sample plugs respectively comprise DNA bands having one of the base pair terminations.

The present invention also extends to an electrophoresis apparatus including the above-described system.

The present invention also provides a method of characterising, in particular sequencing, polymeric samples, comprising the steps of: generating a space-time map of points representative of the signal peaks of signals detected at a plurality of spaced positions as passed by the migrating components of a plurality of separately-provided sample plugs; and identifying vertices from the space-time map, with a single vertex being identified for the components of each separately-provided sample plug and the velocities of the sample components being determinable from the points in the space-time map.

Preferably, the method further comprises the steps of determining the nominal velocities associated with the signal peaks in the signals and grouping those signal peaks into sets according to nominal velocity.

Preferably, a time component corrected according to a function of the electric current variation is utilised in generating the space-time map.

More preferably, the correction is according to the function $t_c = \int I_0/I(t')dt'$ in the range of 0 to t, where t is the measured time, $t_c$ is the corrected time, I is the measured current and $I_0$ is the reference current.

Preferably, the space-time map is an equiphase space-time map of equiphase points.

More preferably, the equiphase points are determined by transforming each data set into a set of local slopes and determining the local minima as the minimum absolute local derivatives.

In one embodiment the components are non-labelled.

In another embodiment the components are labelled.

Preferably, the components are migrated through a channel.

More preferably, the channel comprises a separation channel through which the components are electrophoretically driven.

In one embodiment the sample plugs are provided at spaced time intervals.

In another embodiment the sample plugs are provided at spaced positions.

Preferably, the sample plugs are provided at substantially the same time.

Preferably, the sample plugs respectively comprise DNA bands having one of the base pair terminations.

A preferred embodiment of the present invention will now be described hereinbelow by way of example only with reference to the accompanying drawings, in which:

FIGS. 1 and 2 illustrate an electrophoresis apparatus in accordance with a preferred embodiment of the present invention.

Figure 1:
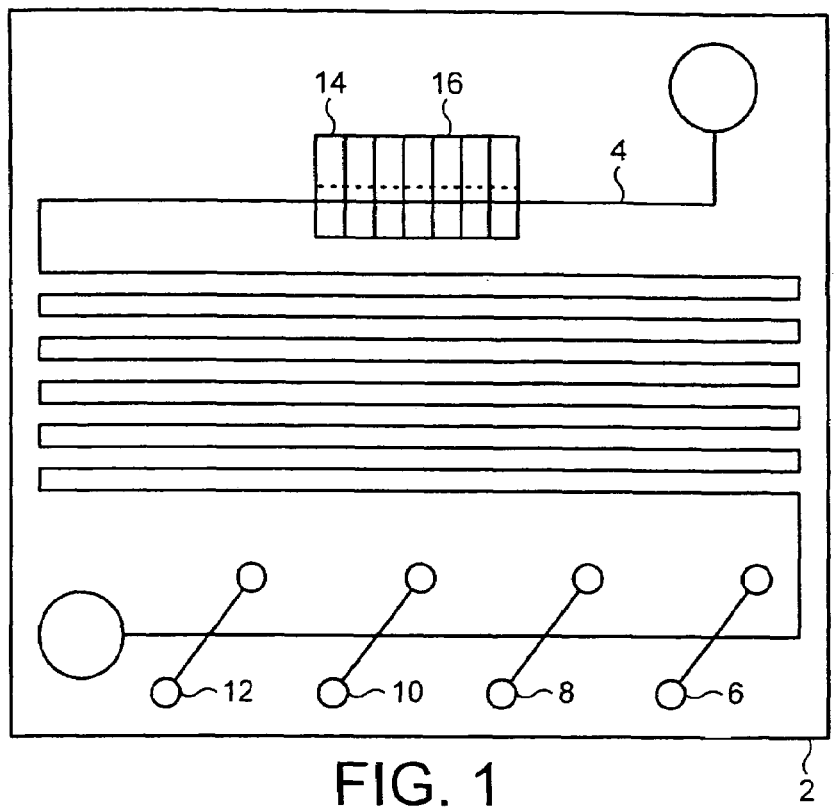
FIG. 1 illustrates the detector chip of an electrophoresis apparatus in accordance with a preferred embodiment of the present invention.
Figure 2:
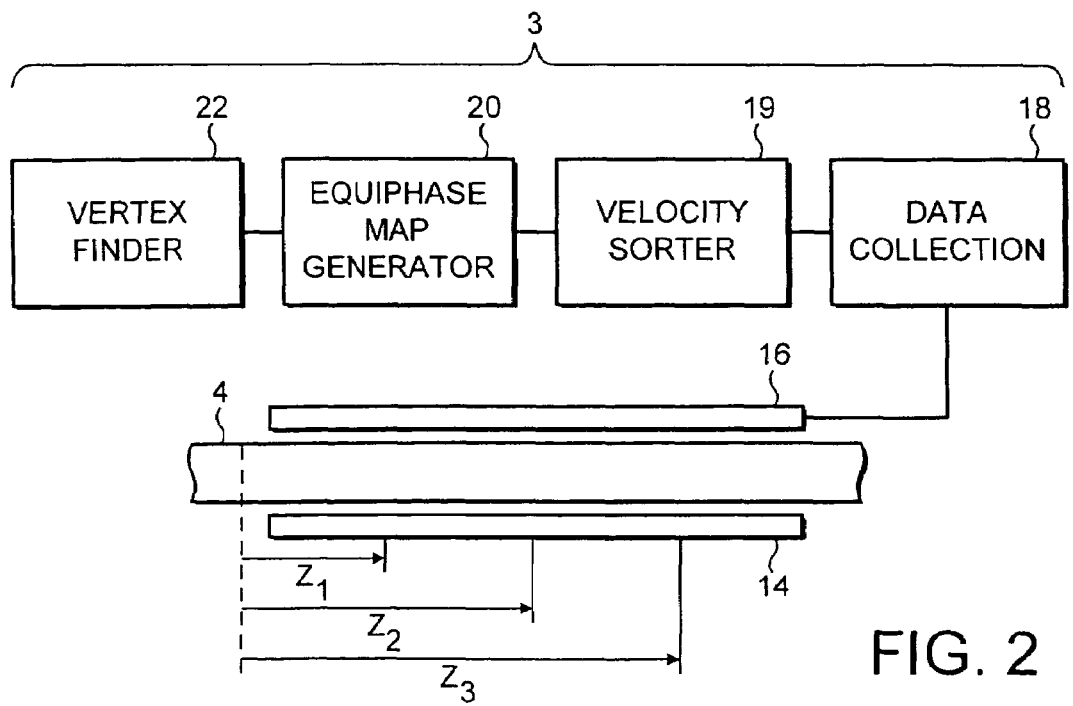
FIG. 2 illustrates the analysis system of the apparatus of FIG. 1.

The electrophoresis apparatus includes a detector chip 2 as microfabricated in a substrate chip, and an analysis system 3 for analysing the detection signals generated by the detector chip 2.

The detector chip 2 includes a separation channel 4, in this embodiment a meandering, gel-filled channel, through which the components of one or more sample plugs are in use driven by an applied electrophoretic voltage. The separation channel 4 has a length sufficient to allow separation of the components of the sample plugs. Preferably, the separation channel 4 has a width of from 25 to 100 μm and a length of from 20 to 300 mm. The separation channel 4 includes a plurality, in this embodiment first to fourth, spaced sample-injection ports 6, 8, 10, 12 through which sample plugs including a plurality of components, in this embodiment DNA bands having the respective base pair terminations A, T, G and C, are separately injected into the separation channel 4.

The detector chip 2 further includes a light source 14, in this embodiment a UV light source, disposed along a length of one side of the separation channel 4, and a detector 16 disposed along the length of the other side of the separation channel 4 to detect light transmitted through the separation channel 4, with the presence of the migrating components being detected by the change in the detected light intensity as caused by absorbtion of the incident light. By detecting the sample components in this manner, the sample components need not necessarily be labelled. In this embodiment the detector 16 comprises a pixel detector array (PDA) which includes a plurality of pixels providing detecting elements for detecting the transmitted light at a plurality of positions $z_1$, $z_2$, $z_3$ spaced along the length of the separation channel 4 and outputting a plurality of signals $S_1$, $S_2$, $S_3$. For ease of description, the detector 16 is illustrated as including three detecting elements at three positions $z_1$, $Z_2$, $Z_3$. It will, however, be understood that in practice the detector 16 comprises a plurality of detecting elements at a plurality of positions $z_1$, $z_2$, $z_3$, ..., $Z_n$, which each output a signal $S_1$, $S_2$, $S_3$, ..., $S_n$. In an alternative embodiment the detector 16 could be provided by a plurality of separate detectors each providing a detecting element. In another alternative embodiment labelled sample components could be used, such as sample components including fluorescent or radioactive labels, which labels would be detected by the detector 16.

The analysis system 3 comprises a data collector 18 for receiving the signals $S_1$, $S_2$, $S_3$ generated by the detector 16 and storing those signals $S_1$, $S_2$, $S_3$ as data sets, a velocity sorter 19 for determining the nominal velocities $v_1$, $v_2$, $v_3$ of the sample components associated with each of the signal peaks $SP_1$, $SP_2$, $SP_3$ of each of the signals $S_1$, $S_2$, $S_3$ and grouping those signal peaks $SP_1$, $SP_2$, $SP_3$ into sets according to nominal velocity, an equiphase space-time map generator 20 for generating an equiphase space-time map of equiphase points from the signal peaks $SP_1$, $SP_2$, $SP_3$ of the signals $S_1$, $S_2$, $S_3$, and a vertex finder 22 for identifying the vertices of the equiphase points of the grouped sets of signal peaks $SP_1$, $SP_2$, $SP_3$. In this embodiment the velocity sorter 19 is provided so as to be operable prior to the equiphase space-time map generator 20. In alternative embodiments the velocity sorter 19 could be provided so as to be operable after the space-time map generator 20 or the vertex finder 22.

Figure 3:
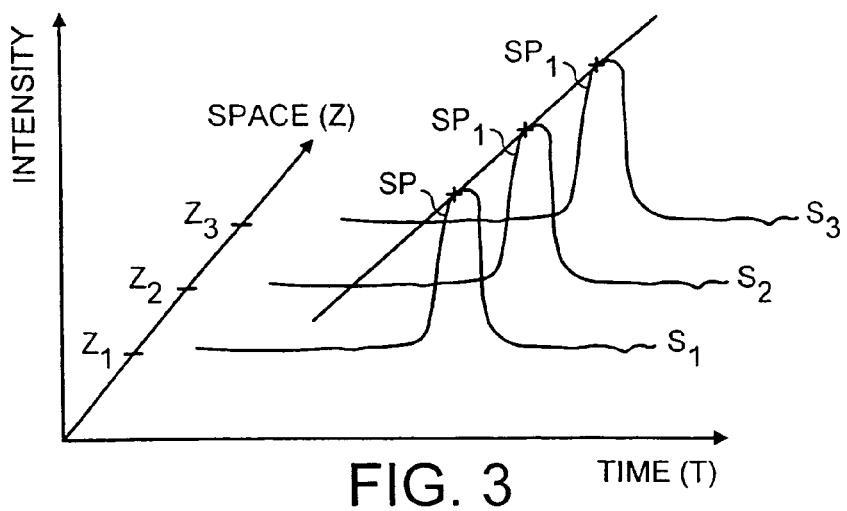
FIG. 3 illustrates a three-dimensional representation of the intensity-time signals of one component of a sample plug as detected at positions $z_1$, $z_2$, $z_3$ spaced along the separation channel of the apparatus of FIG. 1.
Figure 4:
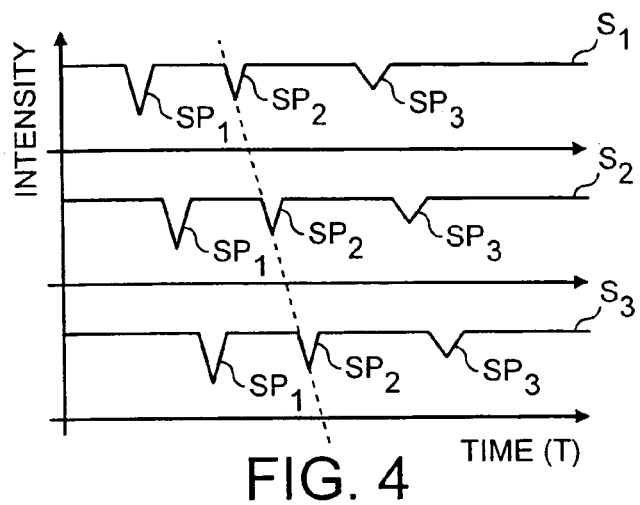
FIG. 4 illustrates the intensity-time signals of three components of a sample plug as detected at positions $z_1$, $z_2$, $z_3$ spaced along the separation channel of the apparatus of FIG. 1.

FIG. 3 is included for the purposes of illustration only and illustrates the signals $S_1$, $S_2$, $S_3$ as including only a single peak $SP_1$, from a single component of a single sample plug. In reality, however, the signals $S_1$, $S_2$, $S_3$ each include a plurality of signal peaks $SP_{1-n}$, $SP_{1-n}$, $SP_{1-n}$. FIG. 4 illustrates the signals $S_1$, $S_2$, $S_3$ as including three signal peaks $SP_1$, $S_2$, $SP_3$ from three components of a single sample plug.

The velocity sorter 19 is configured to determine the nominal velocities $v_1$, $v_2$, $v_3$ of the sample components associated with each of the signal peaks $SP_1$, $SP_2$, $SP_3$ in each of the signals $S_1$, $S_2$, $S_3$ and then group those signal peaks $SP_1$, $SP_2$, $SP_3$ into sets according to nominal velocity. The nominal velocities $v_1$, $v_2$, $v_3$ can be calculated as the positions $z_1$, $Z_2$, $Z_3$ of the detector elements are fixed and the elapsed time t is extractable from the signals $S_1$, $S_2$, $S_3$, where the nominal velocities can be expressed as $v_{1-n} = z_{1-n}/t$. By grouping the signal peaks $SP_1$, $SP_2$, $SP_3$ into sets according to nominal velocity, and hence sample component, subsequent analysis is facilitated as the data points associated with each sample component can be fitted without requiring the use of complex data extraction techniques. Velocity sorting is encompassed by our earlier WO-96/35946, the content of which is incorporated herein by reference.

Figure 5:
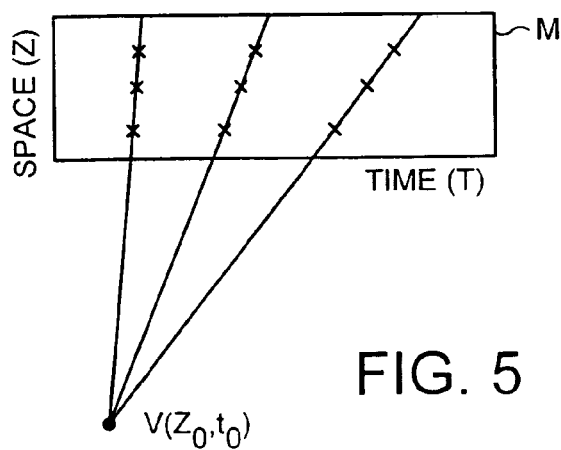
FIG. 5 illustrates a space-time map as generated from the intensity-time signals of FIG. 4.

The equiphase space-time map generator 20 is configured to determine the local minima of the signal peaks $SP_1$, $SP_2$, $SP_3$ in the signals $S_1$, $S_2$, $S_3$ detected at the detection positions $z_1$, $Z_2$, $Z_3$ and generate an equiphase map M in space-time dimensions from the determined local minima. FIG. 5 illustrates the space-time map M generated from the local minima extracted from the signal peaks $SP_1$, $SP_2$, $SP_3$ of the signals $S_1$, $S_2$, $S_3$.

In this embodiment each electropherogram is transformed into a set of local slopes, where a triangular slope sequence defines a signal and the local extreme is the minimum absolute local derivative.

Also, in this embodiment the time component of the detected signals $S_1$, $S_2$, $S_3$ is corrected as a function of the integrated electric current variation. Owing to the variation of various factors in electrophoretic detection, the temperature being one of the most significant, the characteristics of the separation medium, in this embodiment a gel, are altered. Firstly, the resistivity of the gel changes, leading to variations in the potential difference between the electrodes and a given point in the gel and fluctuations in the electric current. Secondly, the sieving properties of the gel change, affecting the mobility of the electrophoresed components. By monitoring the electric current, the time component of the space-time map M can be corrected as set out hereinbelow. Specifically, the time component is curved as a function of the integrated electric current variation.

The velocity of a sample component is:

$$v = dz/dt \qquad (1)$$

For a transformation of the measured time component to a corrected time component $t \to t_c$, it follows that $dt \to dt_c$ and $v \to v_c$. Thus:

$$v_c/v = dt/dt_c \qquad (2)$$

The transformation $v \to v_c$ can be defined as:

$$v_c/v = I(t)/I_0 \qquad (3)$$

where I is the measured current and $I_0$ is the reference current which corresponds to the frame where all velocities and time components are projected.

From equations (2) and (3), it follows:

$$dt_c = I_0/I(t)dt \to t_c = \int I_0/I(t')dt' \text{ for 0 to } t \qquad (4)$$

The justification for the velocity transformation (3) is that the velocity is approximately proportional to the applied electric field, which in turn is proportional to the electric current in the separation channel 4. This correction factor has been found to work well for small current changes, with the integral of equation (4) providing for an accurate time transformation.

The vertex finder 22 is configured, in this embodiment by the use of rotational matrices, to identify the vertices V of the equiphase points of the grouped sets of signal peaks $SP_1$, $SP_2$, $SP_3$ as determined by the equiphase space-time map generator 20, where the components of each injected sample plug have a common vertex V by virtue of being time and/or spatially separated in the space-time dimension. All of the sample components injected in a single sample plug are uniquely identified by a single vertex V in space-time co-ordinates, thus allowing for the identification of the sample components from each of a plurality of separately-provided sample plugs. FIG. 5 illustrates the vertex V as determined from the generated space-time map M. This space-time map includes only a single vertex V as all of the components were provided in a single sample plug.

By using each vertex V as a constraint to extract the velocity spectrum of the sample components, the resolution is approximately proportional to $\sqrt{n}$, where n is the number of components. In this way, the velocity of one component is calculated using the velocities of all of the other components from the same sample plug, and thus, as the number of components in a sample increases, the resolution of the analysis increases accordingly. Such space parameterisation which results in multiple vertex formation in the form of intensity enhanced regions in space-time co-ordinates is particularly suited to the cases of multiple sample injections and multiple column correlation. The power of this technique has been demonstrated on DNA samples which include large numbers of fragments (>100) having lengths of one base pair difference, thereby providing a sequencing technique having a greatly extended dynamic range.

Figure 6:
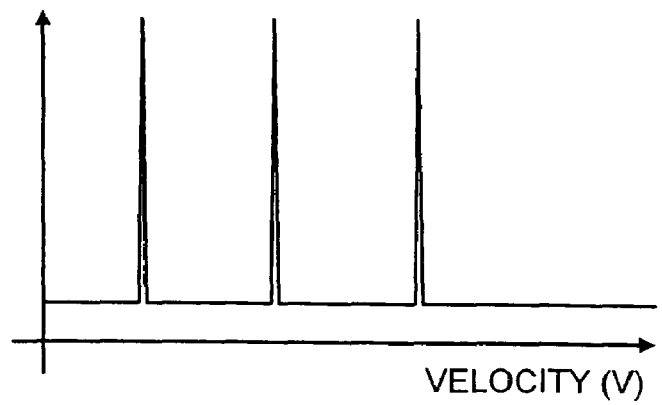
FIG. 6 illustrates the velocity spectrum as determined from the vertexed space-time map of FIG. 5.
Figure 7:
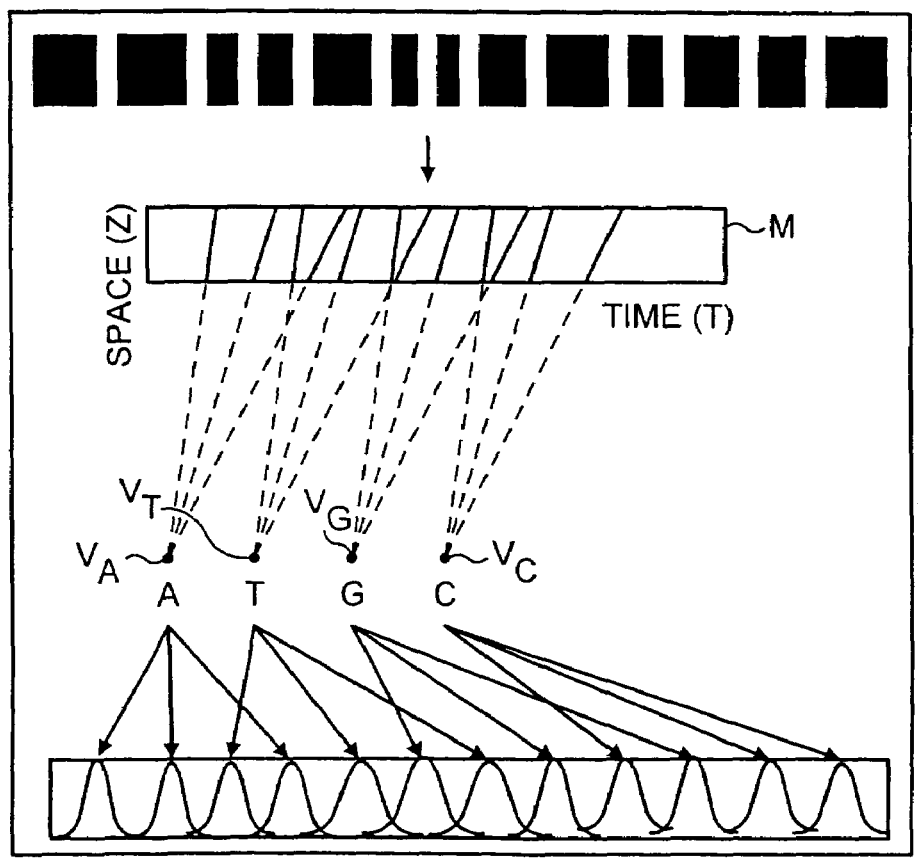
FIG. 7 illustrates a space-time map as generated from the intensity-time signals from four separately-injected DNA sample plugs comprising DNA bands having different base pair terminations.

From the determination of the vertices V in the space-time map M, high resolution of the electrophoresis data is achieved, allowing accurate determination of the velocities of the sample components as illustrated in FIG. 6.

Use of the above-described electrophoresis apparatus to sequence DNA samples having the base pair terminations A, T, G and C will now be described hereinbelow.

In use, four sample plugs comprising DNA bands having different length and one of base pair terminations A, T, G and C are separately introduced into the ports 6, 8, 10, 12 of the separation channel 4, and electrophoretically driven thereaong. In one mode of use, the sample plugs are introduced simultaneously into the ports 6, 8, 10, 12 which are spatially separated along the separation channel 4. In another mode of use, the sample plugs are introduced sequentially into one of the ports 6, 8, 10, 12 so as to be time spaced. The signals $S_1$, $S_2$, $S_3$, ..., $S_n$ detected by the detector 16 as the DNA bands pass the detecting elements at the detecting positions $z_1$, $z_2$, $z_3$, ..., $z_n$ are collected by the data collector 18. The velocity sorter 19 then determines the nominal velocities $v_1$, $v_2$, $v_3$, ..., $V_n$ of the sample components associated with each of the signal peaks $SP_1$, $SP_2$, $SP_3$, ..., $SP_n$ of the signals $S_1$, $S_2$, $S_3$, ..., $S_n$ and groups those signal peaks $SP_1$, $SP_2$, $SP_3$, ..., $SP_n$ into sets according to nominal velocity. The equiphase space-time map generator 20 then determines the local minima of the signal peaks $SP_1$, $SP_2$, $SP_3$, ..., $SP_n$ of the signals $S_1$, $S_2$, $S_3$, ..., $S_n$, and generates an equiphase space-time map M. The vertex finder 22 then identifies the vertices $V_A$, $V_T$, $V_G$, $V_C$ of the determined local minima for each of the grouped sets of signal peaks $SP_1$, $SP_2$, $SP_3$, ..., $SP_n$. In this embodiment the space-time map M includes four vertices $V_A$, $V_T$, $V_G$, $V_C$ as four sample plugs were separately injected into the separation channel 4, each being attributable to DNA bands having one of the base pair terminations A, T, G and C. In this way, the DNA sample can be sequenced, with the lengths of the DNA bands being determined from the migration velocities.

Finally, it will be understood that the present invention has been described in its preferred embodiment and can be modified in many different ways without departing from the scope of the invention as defined by the appended claims.

The invention claimed is:

1. A system for characterising, in particular sequencing, polymeric samples, comprising:
    a space-time map generator for generating a space-time map of points representative of the signal peaks of signals detected at a plurality of spaced positions as passed by the migrating components of a plurality of separately-provided sample plugs; and
    a vertex finder for identifying vertices from the space-time map, with a single vertex being identified for the components of each separately-provided sample plug and the velocities of the sample components being determinable from the points in the space-time map.

2. The system of claim 1, further comprising a velocity sorter for determining the nominal velocities associated with the signal peaks in the signals and grouping those signal peaks into sets according to nominal velocity.

3. The system of claim 1, wherein the space-time map generator is configured to utilize a corrected time component in generating the space-time map according to a function of the electric current variation.

4. The system of claim 1, wherein the space-time map generator is an equiphase space-time map generator for generating an equiphase space-time map of equiphase points.

5. The system of claim 4, wherein the equiphase space-time map generator is configured to transform each data set into a set of local slopes and determine the local extreme as the minimum absolute local derivatives.

6. The system of claim 1, wherein the components are non-labeled.

7. The system of claim 1, wherein the components are labeled.

8. The system of claim 1, wherein the components are migrated through a channel.

9. The system of claim 8, wherein the channel comprises a separation channel through which the components are electrophoretically driven.

10. The system of claim 1, wherein the sample plugs respectively comprise DNA bands having one of the base pair terminations.

11. A method of characterising, in particular sequencing, polymeric samples, comprising the steps of:
    generating a space-time map of points representative of the signal peaks of signals detected at a plurality of spaced positions as passed by the migrating components of a plurality of separately-provided sample plugs; and
    identifying vertices from the space-time map, with a single vertex being identified for the components of each separately-provided sample plug and the velocities of the sample components being determinable from the points in the space-time map.

12. The method of claim 11, further comprising the steps of determining the nominal velocities associated with the signal peaks in the signals and grouping those signal peaks into sets according to nominal velocity.

13. The method of claim 11, wherein a time component corrected according to a function of the electric current variation is utilized in generating the space-time map.

14. The method of claim 11, wherein the space-time map is an equiphase space-time map of equiphase points.

15. The method of claim 14, wherein the equiphase points are determined by transforming each data set into a set of local slopes of the signals detected at a plurality of spaced positions and determining the local extreme as the minimum absolute local derivatives.

16. The method of claim 11, wherein the components are non-labeled.

17. The method of claim 11, wherein the components are labeled.

18. The method of claim 11, wherein the components are migrated through a channel.

19. The method of claim 18, wherein the channel comprises a separation channel through which the components are electrophoretically driven.

20. The method of claim 11, wherein the sample plugs are provided at spaced time intervals.

21. The method of claim 11, wherein the sample plugs are provided at spaced positions.

22. The method of claim 21, wherein the sample plugs are provided substantially at the same time.

23. The method of claim 11, wherein the sample plugs respectively comprise DNA bands having one of the base pair terminations.

24. An electrophoresis apparatus including a system for characterising, in particular sequencing, polymeric samples, comprising: a space-time map generator for generating a space-time map of points representative of the signal peaks of signals detected at a plurality of spaced positions as passed by the migrating components of a plurality of separately-provided sample plugs; and a vertex finder for identifying vertices from the space-time map, with a single vertex being identified for the components of each separately-provided sample plug and the velocities of the sample components being determinable from the points in the space-time map.

25. A system for characterising, in particular sequencing, polymeric samples including a method comprising the steps of: generating a space-time map of points representative of the signal peaks of signals detected at a plurality of spaced positions as passed by the migrating components of a plurality of separately-provided sample plugs; and identifying vertices from the space-time map, with a single vertex being identified for the components of each separately-provided sample plug and the velocities of the sample components being determinable from the points in the space-time map.

* * * * *